(12) United States Patent
Cui et al.

(10) Patent No.: US 7,288,174 B2
(45) Date of Patent: Oct. 30, 2007

(54) ELECTROCHEMICAL BIOSENSOR

(75) Inventors: Gang Cui, Jilin (CN); Jae-Hyun Yoo, Seou (KR); Moon-Hwan Kim, Kyoungki (KR); Ju-Yong Kim, Kyoungki (KR); Jung-Hee Uhm, Seoul (KR); Hakhyun Nam, Kangbuk-ku (KR); Geun-Sig Cha, Seoul (KR)

(73) Assignee: i-SENS, Inc., Seoul (KR)

( * ) Notice: Subject to any disclaimer, the term of this patent is extended or adjusted under 35 U.S.C. 154(b) by 0 days.

(21) Appl. No.: 10/778,685

(22) Filed: Feb. 12, 2004

(65) Prior Publication Data

US 2005/0000808 A1 Jan. 6, 2005

(30) Foreign Application Priority Data

Jun. 9, 2003 (KR) .................... 10-2003-0036804

(51) Int. Cl.
*G01N 27/327* (2006.01)
(52) U.S. Cl. .............................. 204/403.14; 204/403.11
(58) Field of Classification Search ..............................
204/403.01–403.15, 412; 435/4, 10–28, 435/817; 436/528–530, 806; 205/777.5, 205/778, 792
See application file for complete search history.

(56) References Cited

U.S. PATENT DOCUMENTS

| | | | | |
|---|---|---|---|---|
| 4,547,465 | A | * | 10/1985 | Eikenberry .................. 436/170 |
| 4,919,767 | A | * | 4/1990 | Vadgama et al. ............ 205/778 |
| 5,120,420 | A | * | 6/1992 | Nankai et al. .......... 204/403.11 |
| 5,205,920 | A | | 4/1993 | Oyama et al. |
| 5,658,444 | A | | 8/1997 | Black et al. |
| 5,762,770 | A | | 6/1998 | Pritchard et al. |
| 5,798,031 | A | | 8/1998 | Charlton et al. |
| 6,004,441 | A | | 12/1999 | Fujiwara et al. |
| 6,183,771 | B1 | * | 2/2001 | Urtti et al. .................. 424/449 |
| 6,241,862 | B1 | | 6/2001 | McAleer et al. |
| 6,258,329 | B1 | * | 7/2001 | Mutterer et al. ....... 422/186.29 |
| 6,270,637 | B1 | | 8/2001 | Crismore et al. |
| 6,299,757 | B1 | * | 10/2001 | Feldman et al. ............ 205/775 |
| 6,475,372 | B1 | | 11/2002 | Ohara et al. |

(Continued)

FOREIGN PATENT DOCUMENTS

CN 1334460 2/2002

(Continued)

OTHER PUBLICATIONS

Virtual Chembook from Mar. 29, 2003 at http://web.archive.org/web/20030329173440/http://www.elmhurst.edu/~chm/vchembook/553phosglycerides.html.*

(Continued)

*Primary Examiner*—Alex Noguerola
(74) *Attorney, Agent, or Firm*—Klarquist Sparkman, LLP (57) ABSTRACT

There is provided the reagent layer composition that can substantially reduce the measurement bias arising from hematocrits. The addition of fatty acid (4-20 carbons) and quaternary ammonium salt to a commonly used reagent layer composition composed of an enzyme, an electron transfer mediator, and several water soluble polymers not only reduce the hematocrit level-dependent bias but also provide very stable performance for an extended period of time. Disclosed are also various types of sub microliter sample volume electrochemical biosensors that are suitable to use with the reagent layer composition of present invention.

16 Claims, 7 Drawing Sheets

U.S. PATENT DOCUMENTS

| | | | |
|---|---|---|---|
| 6,696,240 | B1 * | 2/2004 | Kloepfer et al. ............ 435/4 |
| 2002/0027072 | A1 | 3/2002 | Cui et al. |

FOREIGN PATENT DOCUMENTS

| EP | 0 359 831 | 8/1995 |
|---|---|---|
| EP | 0 732 406 | 9/1996 |
| EP | 0 735 363 | 10/1996 |
| EP | 1182456 A2 * | 2/2002 |
| EP | 1 202 057 | 5/2002 |
| JP | 1134461 | 5/1989 |
| JP | 02-157646 | 6/1990 |
| JP | 02-231558 | 9/1990 |
| JP | 02-503826 | 11/1990 |
| JP | 2000-338076 | 12/2000 |
| JP | 2001-091512 | 4/2001 |
| JP | 2002-526759 | 8/2002 |
| WO | 97/02487 | 1/1997 |
| WO | 88/09808 | 12/1998 |
| WO | 00/20626 | 4/2000 |
| WO | WO 01/57510 | 8/2001 |
| WO | 02/14535 | 2/2002 |
| WO | 03/563345 | 7/2003 |

OTHER PUBLICATIONS

"n-tridecanoic acid" definition from Hawley's Condensed Chemical Dictionary, 14th Edition, 2002, John Wiley & Sons, Inc.*
"stearic acid" definition from Merriam-Webstaer Online, Nov. 28, 2005.*
"myristic acid" definition from Merriam-Webster Online, Nov. 28, 2005.*
"oleic acid" definition from Merriam-Webstaer Online, Nov. 28, 2005.*
Database Medline [Online] US National Library of Medicine (NLM), Bethesda, MC, US; Sep. 1986, Kaler G V et al.: "[Erythrocyte hemolysis by detergents--a mathematical model and analysis of the concentration and kinetic curves]" XP002300819 Database accession No. NLM3798561.
First Office Action for Chinese Patent Application No. 200410028372.1. Feb. 10, 2006.
Second Office Action for Chinese Patent Application No. 200410028372.1. Sep. 15, 2006.
Search Report for European Patent Application No. 04 100 245.2 - 1223. Jul. 10, 2005.

* cited by examiner

FIG. 4 a: Glucose
b: Glucose + Acetoaminophen (660 mM)
c: Glucose + Ascorbic acid (570 mM)
d: Glucose + Uric acid (916 mM)

ELECTROCHEMICAL BIOSENSOR

CROSS REFERENCE TO RELATED APPLICATIONS

This application claims priority from Korean Patent Application No. 10-2003-0036804, filed Jun. 9, 2003.

FIELD OF THE INVENTION

The present invention relates to electrochemical biosensors. More particularly, the present invention relates to electrochemical biosensor containing reagent layer composition that results in drastically reduced measurement bias arising from hematocrits. The reagent layer composition contains an enzyme, electron transfer mediator, water soluble polymers, a fatty acid (alkyl chain lengths: 4-20 carbons), and a quaternary ammonium salt. Disclosed are also various types of sub microliter sample volume electrochemical biosensors that are suitable to use with the reagent layer composition of present invention.

BACKGROUND OF THE INVENTION

Periodic monitoring of blood glucose levels is needed for the diagnosis and prophylaxis of diabetes mellitus. It is easily performed by individuals using strip-type biosensors designed for hand-held reading devices. Many commercial biosensors exploit the following reaction to quantify the glucose levels in whole blood samples:

(wherein, GOx represents glucose oxidase; $GOx_{-FAD}$ and $GOx_{-FADH2}$ represent an oxidized state and a reduced state of glucose oxidase, respectively; and, $M_{ox}$ and $M_{red}$ denote the oxidized and reduced electron transfer mediator, respectively. As shown in the reaction, glucose is oxidized to gluconic acid by reducing $GOx_{-FAD}$ to $GOx_{-FADH2}$. The reduced glucose oxidase transfers electron(s) to the mediator $M_{ox}$ and to the working electrode. The series of reaction cycle is driven by the anodic potential applied at the working electrode, and the redox current proportional to the level of glucose is measured.

Although electrochemical biosensors are conveniently used for monitoring and controlling the blood glucose levels, their accuracies are greatly affected by the presence of various easily oxidizable species (e.g., ascorbic acid, uric acid, acetaminophen, and etc.) in blood samples. Another serious measurement bias results from blood hematocrits. The interference from oxidizable species may be reduced by employing an electron transfer mediator that has lower oxidization potential than the interfering substances in the reagent layer. However, few practical solutions have been proposed to reduce the measurement bias from blood hematocrits. They teach the use of an additional hematocrit separation or erythrocyte exclusion layer (JP 1134461, JP 2000338076, and U.S. Pat. No. 5,658,444) dispensed on the reagent layer, printable reagent/blood separation paste formulated with a silica filler (U.S. Pat. No. 6,241,862 B1), and a chemometric correction method combined with the double excitation potentials (WO 01/57510 A2). The disclosed methods, however, cannot be realized by simple dispensing of the reagent cocktail on the working electrode, requiring either extra steps to the manufacturing process or a large loss of the reagents in printing the reagent layer.

A large hematocrit level-dependent bias may lead to an erroneous judgment for those who regularly monitor their blood glucose levels with disposable biosensor strips, causing even the loss of their lives.

SUMMARY OF THE INVENTION

It is therefore an object of present invention to provide reagent layer compositions that can be used to prepare the disposable biosensors with drastically reduced hematocrit level-dependent bias. The reagent layer compositions given in this invention can be dispensed in dropwise directly on the working electrode of biosensor strips, which results in the substantially improved manufacturability in mass production.

It is a further object of the present invention to provide various biosensor designs that result in the improved electroanalytical performance when prepared with the present reagent layer compositions.

BRIEF DESCRIPTION OF THE DRAWINGS

The application of the preferred embodiments of the present invention is best understood with reference to the accompanying drawings, in which like reference numerals are used for like and corresponding parts, wherein.

DETAILED DESCRIPTION OF THE INVENTION

The electrochemical biosensor of the present invention comprises: a) a lower and upper substrates; b) a working electrode and a reference (or counter) electrode respectively formed on either the lower substrate or the upper substrate; c) a reaction layer containing enzyme, electron transfer mediator, water soluble polymers and a fatty acid or its salt formed over the working electrode; and d) a spacer formed between the lower and the upper substrates, wherein the spacer is provided with a cut out pattern of a sample introducing bay, an air discharge channel, and a void at the cross of sample introducing bay and air discharge channel.

The electrochemical biosensor strip of present invention comprises: a) lower and upper substrates (typically polymeric films) on which working and auxiliary (counter or reference) electrodes are formed by screen printing or deposition of conducting materials (e.g., carbon or metal pastes, metal vapor, and conducting polymer); b) a Γ-shaped sampling channel enclosed between the two substrates separated by a double-sided adhesive spacer; c) a reagent layer that provides substantially reduced hematocrit level-dependent bias.

The electrode systems may be prepared on the same base substrate or on both lower and upper substrates: i.e., (1) a working electrode and an auxiliary electrode (or a reference electrode) formed on the same base substrate; and (2) a working electrode and an auxiliary electrode formed respectively on the base and cover substrates and arranged to face each other (converse-type electrodes: see, E. K. Bauman et al., Analytical Chemistry, vol 37, p 1378, 1965; K. B. Oldham in "Microelectrodes: Theory and Applications," Kluwer Academic Publishers, 1991.). An extra electrode may be provided on the base substrate behind the working electrode to measure the fluidity of whole blood samples. Since hematocrits change the fluidity and electrical conductivity of blood, sampling times through a capillary channel of biosensor strips vary proportionally with the level of hematocrits in whole blood samples. Such variances in fluidity of blood samples may be used to correct the hematocrit level-dependent bias in the blood glucose measurements.

The Γ-shaped sampling channel enables a rapid, accurate and convenient introduction of a blood sample from the tip of the biosensor strips. The sampling introducing channel comprises a sample introducing bay, an air discharge channel, and a void, wherein the sample introducing bay is crossed with the air discharge channel below the bay end, leaving a void space at the cross. The void helps holding constant and accurate sample volume for the measurement within the bay, discharging the excess sample through the air discharge channel, and also be utilized further to place a fluidity determining electrode.

The reagent layer of present invention is formed on the working electrode of biosensor strip simply by dispensing a reagent layer composition solution containing an enzyme (e.g., glucose oxidase, lactate oxidase, etc.), electron transfer mediator, water soluble polymers (e.g., cellulose acetate, polyvinyl alcohol, polypyrrol, etc.), and a hematocrit interference reducing agent (fatty acids with 4-20 carbon alkyl chain), and a lipophilic quaternary ammonium salt.

Further, the biosensor of the present invention comprises a viewing window on the upper substrate which is located at the crossing cover of the sample channel. The viewing window can show the fluidity determining electrode on lower substrate through a part of upper substrate for sample fill.

Figure 1:
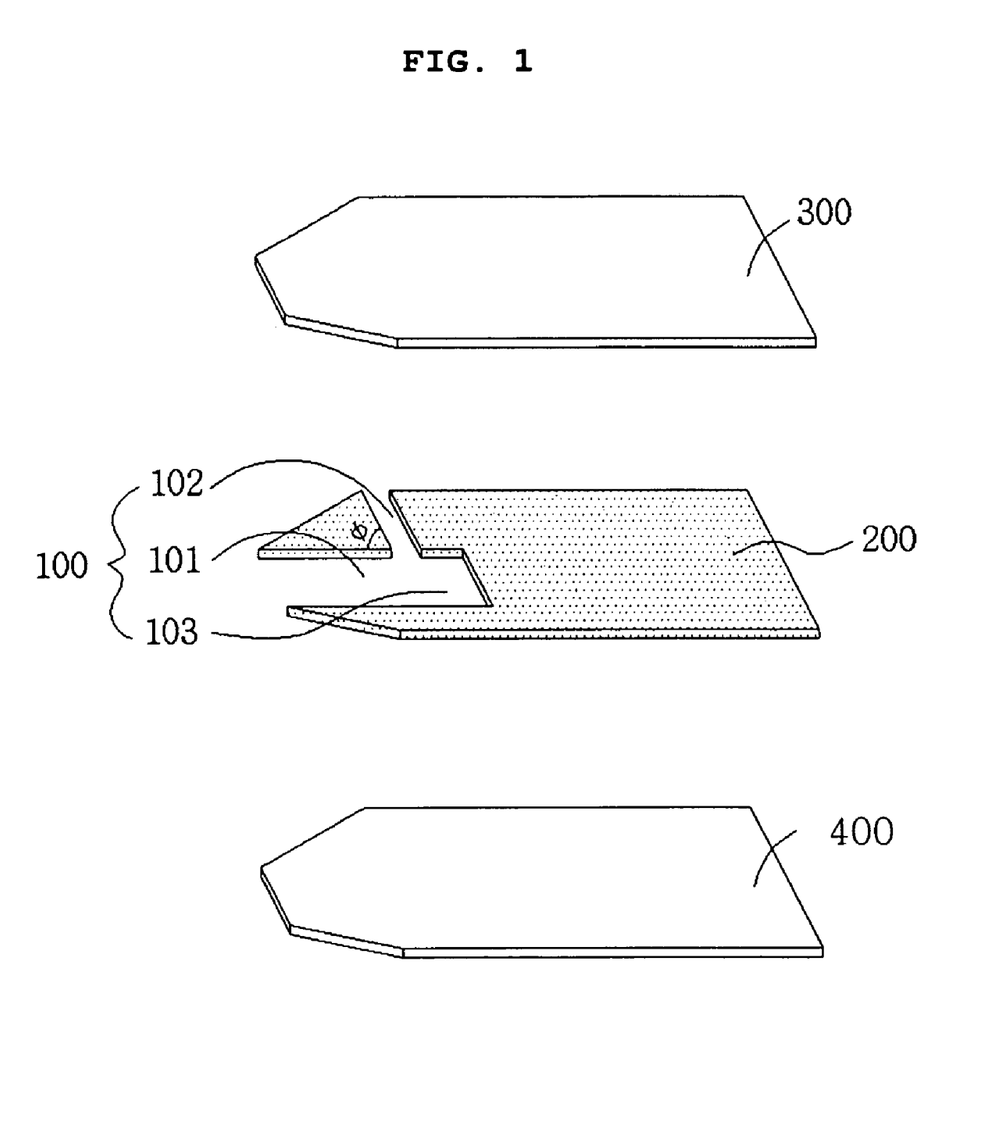
FIG. 1 is an exploded perspective view, which illustrates an electrochemical biosensor with a sample introducing part according to the present invention.

With reference to FIG. 1, an electrochemical biosensor comprises a spacer 200 and a lower substrate 400 and an upper substrate 300 for forming the electrochemical sensors and sample introducing channel. Formed into one end of the spacer 200 is a sample introducing bay 101, an air discharge channel 102, and a void 103. Notably, the sample introducing bay 101, a narrow channel patterned in the middle of the strip, communicates with the air discharge channel 102 in a roughly perpendicular manner slightly below the end of the bay-shaped channel, forming the void 103 behind the point of communication. Taken as a whole, the sample introducing bay 101, air discharge channel 102, and void 103 constitute a sample introducing part 100.

The sample introducing bay 101 is a passage capable of introducing the sample into the biosensor, and the air discharge channel 102 is a passage for air. Due to capillary action, a sample to be tested is introduced into the sample introducing part 100 and an air is discharged through the air discharge channel 102.

The void 103 provides for the vacant position and reduces an air-pocket phenomenon, which often occurs at the point of communication between the sample introducing bay 101 and the air discharge channel 102. The occurrence of the air-pocket phenomenon results in inaccurate measurements such that the void 103 ensures accurate and reproducible sampling.

The ratio between the widths of the air discharge channel 102 and the sample introducing bay 101(The ratio of the width of the air discharge channel 102 to that of sample introducing bay 101) is no more than 1:2. The most preferable range is 1:5 to 1:2. A ratio below 1:2 ensures the containment of an exact amount of sample in sample introducing bay 101 with minimal fill over through the air discharge channel 102.

In FIG. 1, the angle of communication (φ) between the sample introducing bay 101 and the air discharge channel 102 is shown as 90°. But, according to another embodiment of the present invention, this angle may be varied within a range of from about 45° to about 135°, preferably, from about 75° to about 105°.

As also shown in FIG. 1 the void 103 extends beyond the point of communication from the sample introducing bay 101. To ensure an exact amount of sampling with no bubble formation, hydrophilic treatment of the sample introducing bay 101 including the void 103 is desired.

The sample introducing part 100 of the present invention has a capacity to introduce 0.1-3.0 μl of a sample. More preferably, this capacity is 0.1-1.0 μl; most preferably, the capacity is 0.3-0.7 μl. Samples less than 0.1 μl are too small to give an accurate measurement within the current biosensor's range of error. Meanwhile, samples greater than 3.0 μl are excessive. In preferred embodiments, accurate measurements have been obtained with samples of just 0.5 μl.

Pressing an organic polymer film consisting of polyester, polyvinyl chloride, or polycarbonate could make the introduction of the spacer 200 between the lower and upper substrate. It could be fabricated by pressing a double-sided adhesive film made of organic polymer, or screen-printing a layer of adhesive with the pattern shown in FIG. 1.

The working principle of the sample introducing part 100 is described in detail as follows.

First, the sample is introduced to the sample introducing bay 101, by way of capillary action, as soon as the sample comes into contact with the mouth of the sample introducing bay 101, and the sample introducing bay 101 is filled with the sample up to the void 103. Extra sample is then forwarded to the air discharge channel 102. Herein, the sample fill-over can be minimized by controlling the ratio of the width of the air discharge channel 102 to that of the sample introducing bay 101 to less than 1:2, and the hydrophilic void 103 removes the air-pocket forming phenomenon occurring at the point of communication between the sample introducing bay 101 and the air discharge channel 102.

According to the preferred embodiment of the present invention, given a 0.5 μl sample capacity, the sample introducing part 100 fills with blood in about 200-2000 ms depending on the hematocrit level, sample storage conditions, and the type of anti-coagulant used. Fresh blood samples normally fills the 0.5 μl sampling channel in about 200-800 ms as a function of hematocrit level.

The sample introducing part 100 of the present invention may be applied to various types of biosensors, including a flat type biosensor (whose electrodes are formed only on lower substrate), a converse type biosensor (whose working and counter electrodes are formed separately on lower and upper substrates, a differential flat type biosensor, a differential converse type biosensor, or a converse biosensor with fluidity determining electrode.

Figure 2:
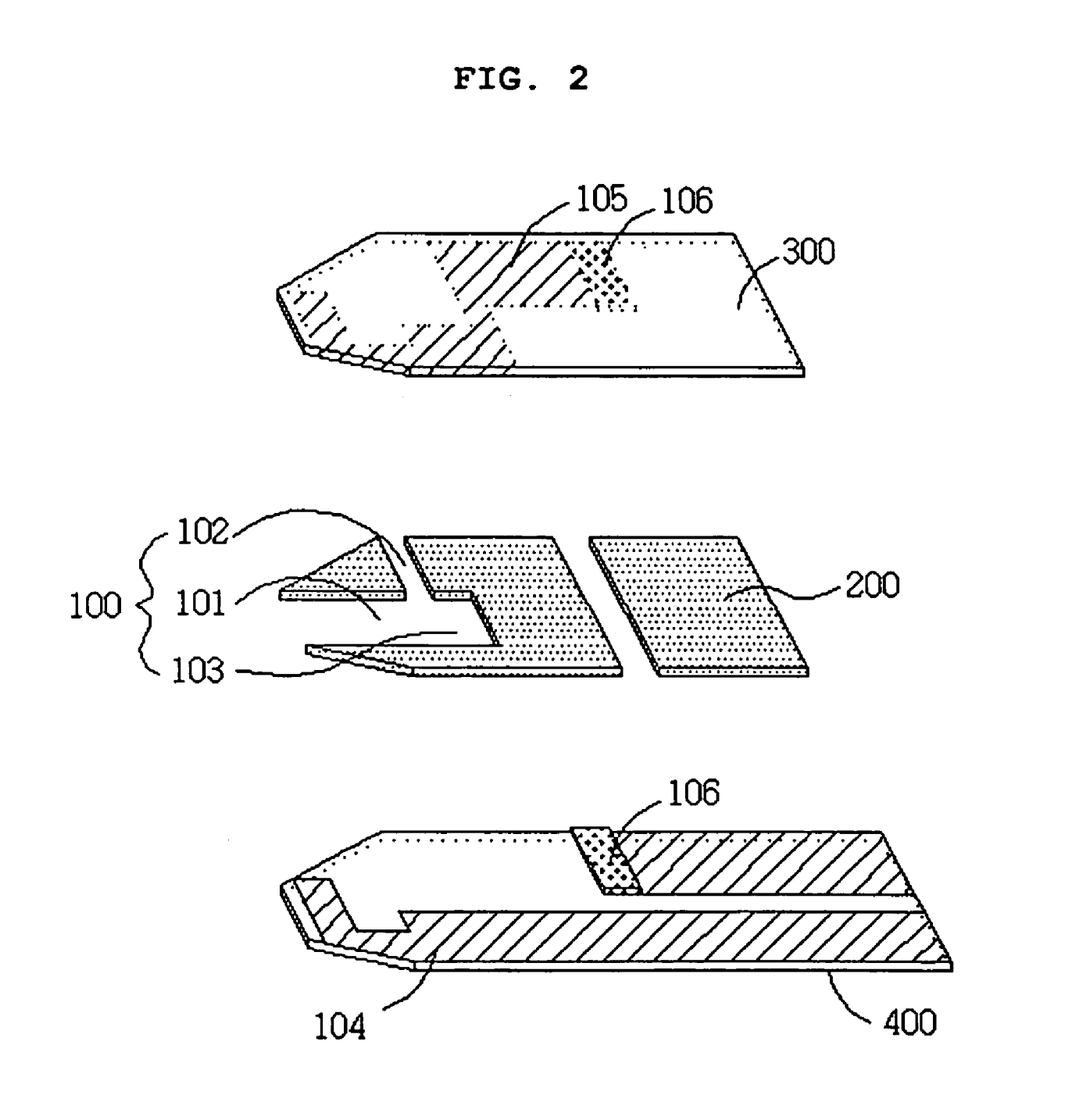
FIG. 2 is an exploded perspective view showing a converse electrode type biosensor constructed in accordance with a preferred embodiment of the present invention.

FIG. 2 illustrates a converse-type biosensor with a sample introducing part 100, characterized in that a lower substrate 400 on which a working electrode 104 and an electrode connector 106 are printed, and an oxidase and an electron transfer mediator are immobilized on the working electrode 104; a sample introducing spacer 200 having the sample introducing part 100; and an upper substrate 300 on which a reference electrode 105, and an electrode connector 106 are printed on the bottom side. The sample introducing part 100 may be formed as shown, but the present invention is satisfied as long as the sample introducing bay 101 communicates with the air discharge channel 102 and the void 103 is formed at the point of communication; the structure of the void 103 may also be modified as detailed above.

The fabrication of the converse type biosensor with the sample introducing part 100 can be accomplished in the same manner as the flat type biosensor with the sample introducing part 100.

Figure 3:
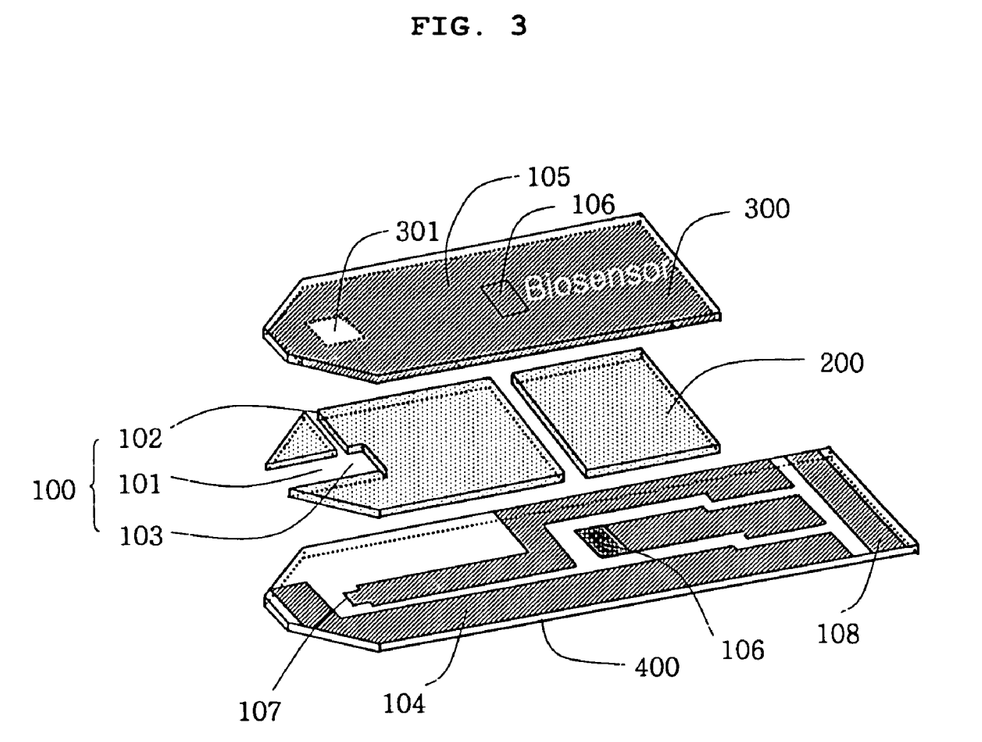
FIG. 3 is an exploded perspective view, which illustrates a converse type electrochemical biosensor with a sample introducing part and a fluidity determining electrode according to the present invention.

As shown in FIG. 3, illustrated is a converse type biosensor with sample fluidity determining capacity, characterized in that lower substrate 400 on which a working electrode 104, an electrode connector 106, fluidity determining electrode 107, and the biosensor identification electrode 108 are printed, and an oxidase and an electron transfer mediator are immobilized on the working electrode 104; a sample introducing spacer 200 having the sample introducing part 100; and an upper substrate 300 on which a reference electrode 105, and an electrode connector 106 are printed on the bottom side. Note that the reference electrode may be printed on whole upper substrate except the area for viewing window 301 for sample fill and the trade mark of the strip, providing more elegant outlook. The sample introducing part 100 may be formed as shown, but the present invention is satisfied as long as the sample introducing bay 101 communicates with the air discharge channel 102 and the void 103 is formed at the point of communication; the structure of the void 103 may also be modified as detailed above. The fluidity of a sample is determined as a function of sample filling speed between the first contact point of electrode 105 near the sample introducing mouth and the fluidity determining electrode 107 which is located either at the void 103 or at the air discharge channel 102.

The substrates of any of the lower or upper substrate for use in the biosensors described above may be made of ceramic, glass, or polymeric materials, with a preference for an organic polymer of polyester, polyvinyl chloride, or polycarbonate. The fabrication of the electrodes, such as the reference electrodes, working electrodes, and auxiliary electrodes, may be achieved using a conductive material, e.g., silver epoxy, silver/silver chloride, carbon, redox couples, or a modified conductive carbon paste containing a resin binder. These materials may be formed into reference, counter, and working electrodes by a screen-printing method, a vapor deposition method followed by etching, or an adhesion of a conductive tape.

The above-described biosensors with the sample introducing part 100 have several advantages.

(1) The air-pocket phenomenon, occurring at the point of communication between the sample introducing bay and air discharge channel, is eliminated while the sample is rapidly introduced into the biosensor.

(2) As the sample introducing part 100 is well enclosed by the narrow mouth and air discharge channel, the biosensors of the present invention maintain a consistent sample concentration with minimal evaporation, thus improving analytical reproducibility. In addition, the sample is better contained with the present invention than other types of sample introducing schemes when the strips are adapted to and removed from instruments, thereby considerably reducing the possibility of contamination.

(3) The biosensors equipped with the sample introducing part 100, in which the sample introducing bay and air discharge channel communicate in a roughly perpendicular manner, are capable of rapidly introducing a predetermined amount of sampled blood and increasing accuracy and reproducibility.

(4) The present invention allows easier blood sampling through the tip of the biosensor when it is applied to body parts.

The reagent layer is formed on the working electrode simply by dispensing a drop (about 300-500 nL) of reagent layer composition solution. The reagent layer composition solution may contain an enzyme (oxidase, esterase or dehydrogenase) for target analyte, an electron transfer mediator, various water soluble polymers, and hematocrit interference reducing agents.

For blood glucose measurement biosensor system, glucose oxidase or glucose dehydrogenase may be used. Herein, it should be understood that the present invention, although described for biosensors for analysis of blood glucose levels, can introduce appropriate enzymes and electron transfer mediators to the electrode system so that a variety of samples, including bio-materials, such as metabolites, e.g., cholesterol, lactate, creatinine, proteins, hydrogen peroxide, alcohols, amino acids, and enzymes, e.g., GPT (glutamate pyruvate transaminase) and GOT (glutamate oxaloacetate transaminase), environmental materials, agricultural and industrial materials, and food materials can be quantitatively analyzed. For instance, cholesterol, lactate, glutamate, hydrogen peroxide, and alcohol can be quantitatively analyzed using glucose oxidase, lactate oxidase, cholesterol oxidase, glutamate oxidase, horseradish peroxidase, or alcohol oxidase, respectively.

The electron transfer mediator provided for the working electrode may employ ferrocene or its derivatives, quinone or its derivatives, organic conducting salts, or viologen. Preferably, the electron transfer mediator is a mixed-valence compound capable of forming redox couples, including hexaamineruthenium (III) chloride, potassium ferricyanide, potassium ferrocyanide, dimethylferrocene, ferricinium, ferocene-monocarboxylic acid, 7,7,8,8-tetracyanoquinodimethane, tetrathiafulvalene, nickelocene, N-methylacidinium, tetrathiatetracene, N-methylphenazinium, hydroquinone, 3-dimethylaminobenzoic acid, 3-methyl-2-benzothiazolinone hydrazone, 2-methoxy-4-allyiphenol, 4-aminoantipyrin, dimethylaniline, 4-aminoantipyrene, 4-methoxynaphthol, 3,3',5,5'-tetramethylbenzidine, 2,2-azino-di-[3-ethylbenzthiazoline sulfonate], o-dianisidine, o-toluidine, 2,4-dichioro phenol, 4-aminophenazone, benzidine, and Prussian blue. Of those, hexaamineruthenium (III) chloride is a preferred electron transfer mediator for the proposed biosensor system, since it satisfies several conditions: (1) both an oxidized and a reduced states thereof in aqueous solution are stable and reversible; (2) the reduced electron transfer mediator is non-reactive to oxygen; (3) its formal potential is low enough to minimize the influence of interfering materials such as ascorbic acid, uric acid, and acetaminophen; (4) the oxidation of the reduced electron transfer mediator is not sensitive to PH; and (5) it does not react with electrochemically interfering materials, such as ascorbic acid, acetaminophen, and uric acid.

Water soluble molecules (0.1-10 wt % in solid components before dissolving in PBS buffer, pH 6.5) are selected from water soluble polymers, the group consisting of polyvinyl pyrrolidone (PVP), polyvinyl alcohol (PVA), perfluoro sulfonate, hydroxyethyl cellulose (HEC), hydroxypropyl cellulose (HPC), carboxy methyl cellulose (CMC), cellulose acetate, polyamide, etc. . The water soluble molecules are added to the reagent layer composition solution to help disperse or stabilize the enzyme. PVP and HPC are preferred for preparing the reagent layer composition solution of present invention.

A fatty acid with a linear alkyl chain of 4-20 carbons may be dissolved in water or a water miscible solvent, and added to the reagent solution in 0.1-20 wt % of all solid components. It is preferred to use a saturated fatty acid or its salt with an alkyl chain of 6-12 carbons: they include caproic acid, heptanoic acid, caprylic acid, nonanoic acid, capric acid, undecanoic acid, and lauric acid. The addition of a fatty acid greatly helps reducing the hematocrit level-dependent bias. On the other hand, the fatty acid tends to shorten the linear dynamic range of a biosensor, especially in the high concentration region.

The quaternary ammonium salt such as the halide compounds of dodecyltrimethylammonium, myristyltrimethylammonium, cetyltrimethylammonium, octadecyltrimethylammonium, tetrahexylammonium, etc. with the fatty acid remedies the problem, while substantially reducing the hematocrit level-dependent bias. The quaternary ammonium salts are added to the reagent layer composition solution in 0.1~30 wt % of all components.

A better understanding of the present invention may be given with the following examples which are set forth to illustrate, but are not to be construed to limit the present invention.

EXAMPLE 1

Preparation of the Reagent Layer Composition Solution Without Fatty Acid

A mixture containing 30 mg of hexaamineruthenium (III) chloride (41.6 wt %), 1 mg of carboxymethylcellulose(1.4 wt %), 1 mg of Triton X–100(1.4 wt %), and 40 mg of glucose oxidase (55.6 wt %) was dissolved in 1 ml PBS buffer solution (pH 6.5)(pH 6.4), and filtrated to eliminate particulates left in solution. The reagent solution was placed in the syringe of a pneumatic dispenser (EFD XL100)

EXAMPLE 2

Preparation of the Reagent Layer Composition Solution with Fatty Acid

A mixture containing 30 mg of hexaamineruthenium (III) chloride(32.6 wt %), 1 mg of carboxymethylcellulose(0.8 wt %), 5 mg of polyvinyl pyrrolidone(4 wt %), 1 mg of Triton X–100(0.8 wt %), 20 mg of lauric acid(15.7 wt %), 30 mg of myristyltrimethylammonium bromide(23.6 wt %), and 40 mg of glucose oxidase (31.5 wt %) was dissolved in 1 ml PBS buffer solution (pH 6.4), and filtrated to eliminate particulates left in solution. The reagent solution was placed in the syringe of a pneumatic dispenser (EFD XL100).

EXAMPLE 3

Fabrication of a Converse Type Two-Electrode Biosensor

As shown in FIG. 2, a working electrode 104 and an electrode connector 106 were screen-printed with conductive carbon paste, and a curing was carried out at 140° C. for five minutes. Then, a circuit connector was screen-printed with the silver paste on one end of the electrode connector 106. The upper substrate with the printed electrode as a reference (auxiliary) electrode 105 was screen-printed with carbon paste and was cured. Finally, the biosensor was fabricated such that the end of the reference electrode 105 was screen-printed with silver paste to be the circuit connector.

The sample introducing spacer 200 comprising the sample introducing bay 101, air discharge channel 102, and the void 103 was placed on the lower substrate by pressing double-sided tape made of polyester. The ratio of the width of the air discharge channel 102 to that of the sample introducing bay 101 was 2:1, and the total amount of sampled blood within the sample introducing part 100 was adjusted to 0.5 µl.

The reagent layer composition solution of Example 1 or Example 2 was applied to the working electrode 104, and was allowed to dry for thirty minutes at 45° C.

Pressing the upper substrate 300 onto the sample introducing spacer 200, so as to connect with the circuit connector of the reagent dispensed lower substrate 400, completed the biosensor shown in FIG. 2.

EXAMPLE 4

Fabrication of Biosensor with Fluidity Determining Electrode

The biosensor with fluidity determining electrode 107 was the converse type biosensor, which was prepared in the same manner as illustrated in Example 3 except that the counter electrode was printed all over the upper substrate (FIG. 3). The tip of the fluidity-determining electrode was placed at the void 103 of the sample introducing part.

The reagent layer composition solution of Example 1 or Example 2 was applied to the working electrode 104, and was allowed to dry for thirty minutes at 45° C.

Pressing the upper substrate 300 onto the sample introducing spacer 200, so as to connect with the circuit connector of the reagent dispensed lower substrate 400, completed the biosensor shown in FIG. 3.

EXPERIMENTAL EXAMPLE 1

Influence of Interfering Materials on a Converse Type Glucose Sensor

Influence of interfering materials such as ascorbic acid, acetaminophen or uric acid, on a converse type glucose sensor fabricated as depicted in example 3 was measured by the following experiment. The mean volume of glucose sensor was 0.5 µl.

Particularly, the total response currents to (a) phosphate buffer (pH 6.4)(pH 7.4) standard solutions containing 177 mg/dL of glucose, (b) phosphate buffer solution containing 177 mg/dL of glucose+660 µM of acetaminophen, (c) phosphate buffer solution containing 177 mg/dL of glucose+570 µM of ascorbic acid, or (d) phosphate buffer solution containing 177 mg/dL of glucose+916 µM of uric acid were measured, respectively. The currents were measured by reading the chronoamperometric response 5 seconds after applying the +0.2 V potential to the working electrode 104 (vs. reference electrode). The results were shown in FIG. 4.

Figure 4:
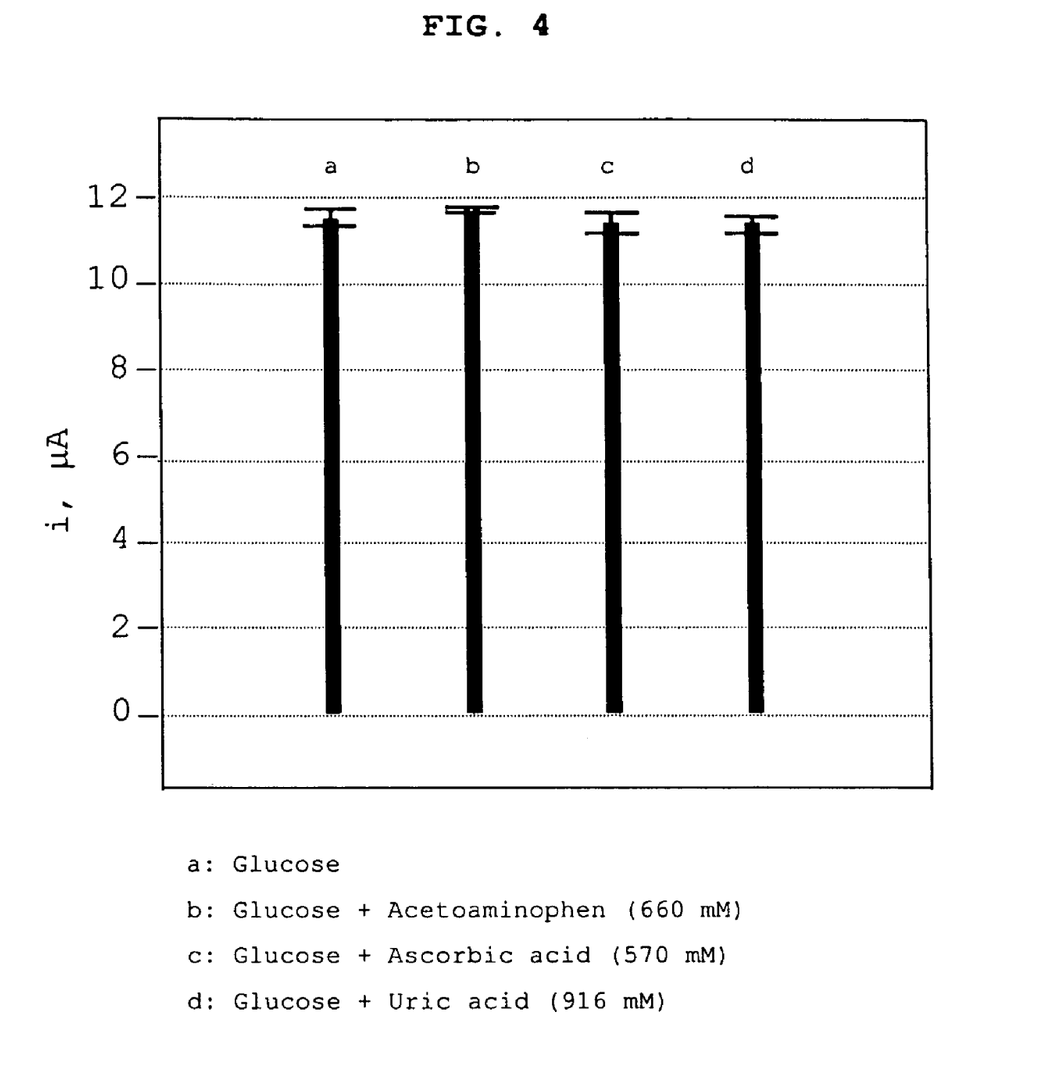
FIG. 4 is the graph that shows the influence of various interfering materials on a converse type glucose sensor: (a) Glucose; (b) Glucose+Acetaminophen (660 µM); (c) Glucose+Ascorbic acid (570 µM); (d) Glucose+Uric acid (916 µM)

FIG. 4 shows that the sensors are affected insignificantly by the presence of interfering materials at an applied potential of +0.2 V.

EXPERIMENTAL EXAMPLE 2

Calibration Curve of a Converse Type Glucose Sensor to Glucose Standard Solutions The converse type glucose sensor prepared in Example 3 was assayed for sensitivity with glucose standard solutions.

Figure 5:
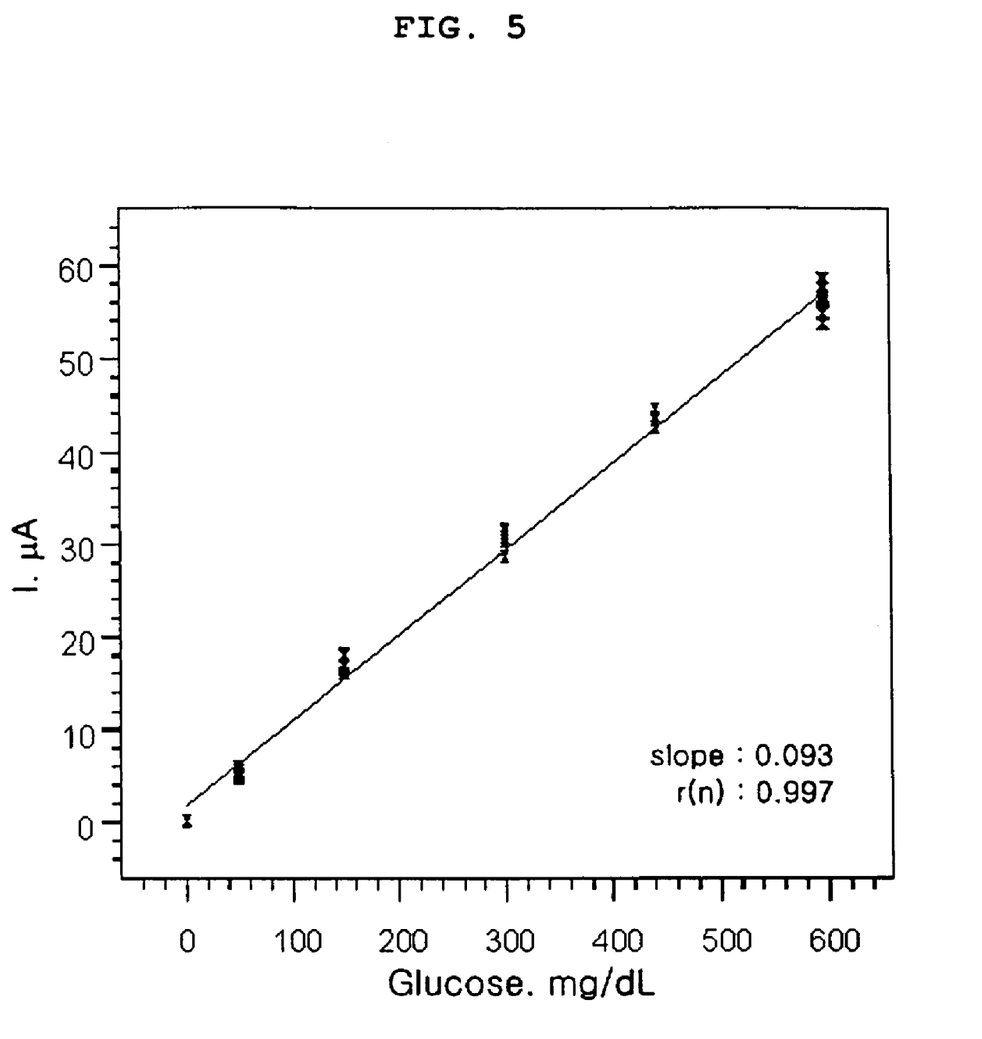
FIG. 5 is a graph showing a calibration curve of a converse type glucose sensor, for sensitivity to glucose standard solution.

Particularly, current values were measured ten times at each concentration 0, 50, 150, 300, 450 or 600 mg/dL under the electrical field of an applied potential of 0.2 V with respect to the reference electrode. The amount of samples applied to the sample introducing part was 0.5 µl and the filling time was no more than 200 ms. The measurements were performed 2 seconds after introducing the sample by applying 0.2 V for three seconds, and the current values were read in five seconds. The calibration curve thus obtained is depicted in FIG. 5.

Figure 6:
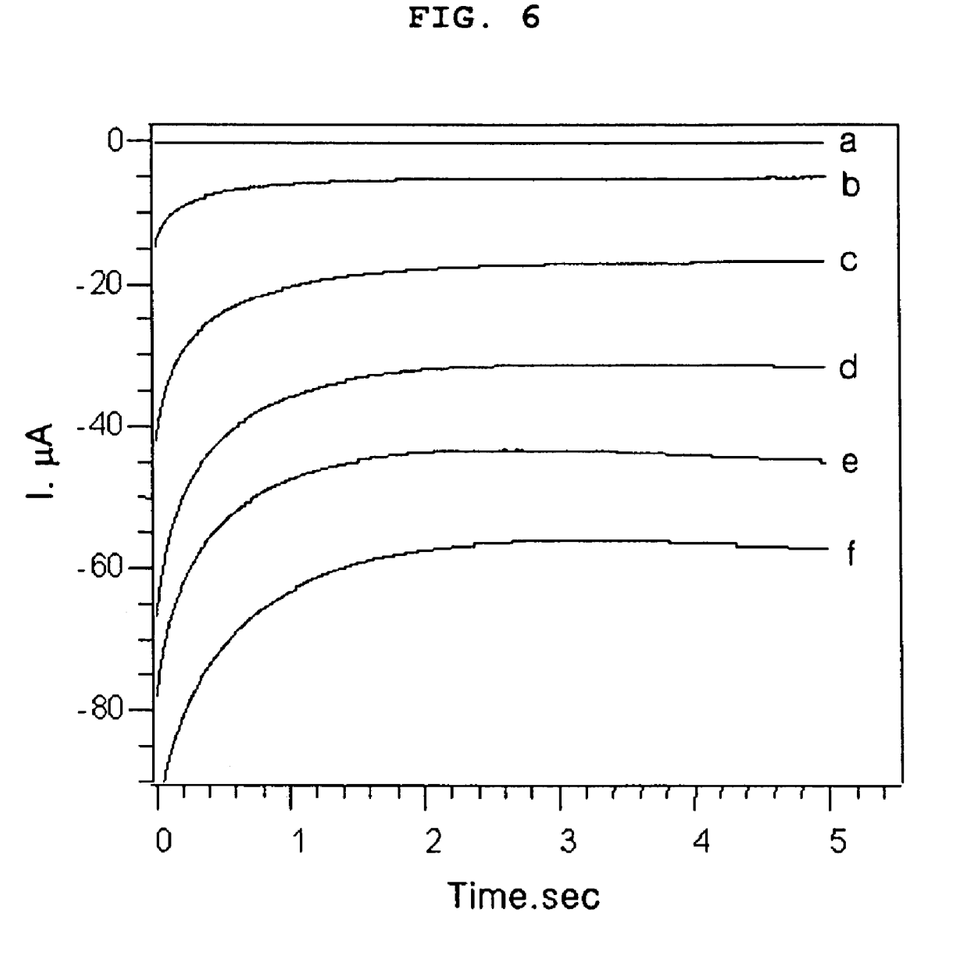
FIG. 6 is a graph showing dynamic curves, obtained by a chronoamperometric method, of a converse type glucose sensor, for glucose standard solutions.

The dynamic curves thus obtained are depicted in FIG. 6, wherein the respective curves show glucose concentrations of 0 mg/dL (curve a), 50 mg/dL (curve b), 150 mg/dL (curve c), 300 mg/dL (curve d), 450 mg/dL (curve e), and 600 mg/dL (curve f). As shown in FIG. 6, The slope was 0.093 [µA/(mg/dL)] and the correlation coefficient was 0.997. From these results, it was confirmed the electrochemical biosensor had excellent linear sensitivity (FIG. 5).

EXPERIMENTAL EXAMPLE 3

Measurement of the Blood Fluidity and Hematocrit Bias Correction

Figure 7:
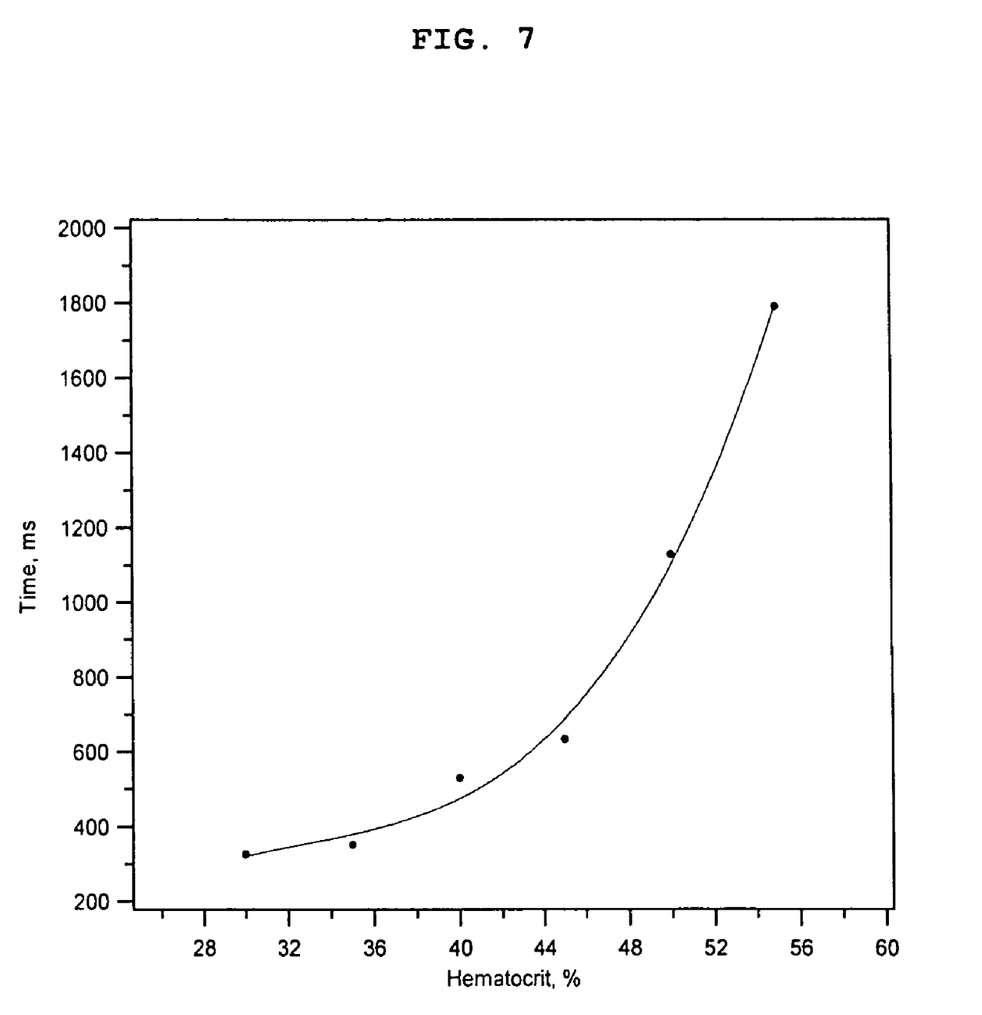
FIG. 7 is a graph that illustrates the relationship between the sample fluidity (as a function of time) and the hematocrit level.

The biosensor equipped with fluidity determining electrode was prepared as described in Example 4. 200 mV of potential was applied to the working electrode 104 and the fluidity determining electrode 107 (vs. the reference electrode 105). When blood samples are introduced through the sample introducing bay 101, a sudden change in current is detected, and the time measurement begins. As soon as the sample reaches the void 103, the second surge of current is detected and the time interval between the first and second surge of current is recorded. The relationship between the sample introducing time and hematocrit level is shown in FIG. 7. The experiment was performed with the sodium fluoride treated whole blood containing 180 mg/dL of glucose and varying hematocrit levels.

The fitting equation was obtained by the above result.

$$Y=-72.23+0.58691X-0.00084073X^2-1.1211\times10^{-6}X^3+5.7521\times10^{-9}X^4-9.1172\times10^{-12}X^5.\quad\text{[mathematical formula 1]}$$

(where Y is the estimated hematocrit level from the sample filling time X measured with the fluidity determining electrode.

Table 1 shows the level of hematocrit estimated from the speed of sample filling time.

TABLE 1

Hematocrit level estimated from the sample filling time of the biosensor prepared in Example 4.

| Hematocrit (%) Prepared sample | Speed (ms) | Estimated Hematocrit (%) |
|---|---|---|
| 30% | 326 | 30.3% |
| 35% | 352 | 32.8% |
| 40% | 530 | 41.8% |
| 45% | 634 | 44.0% |
| 50% | 1129 | 50.1% |
| 55% | 1791 | 54.7% |

In a separate experiment, calibration curves were obtained with the whole blood at various hematocrit levels and the relationship between the hematocrit level and the response slopes was formulated (Table 2).

TABLE 2

Calibration curves at different hematocrit levels.

| Hematocrit | Equation (y = current µA; x = glucose) |
|---|---|
| 30% | y = 0.035934 x − 1.7228 |
| 35% | y = 0.030559 x − 1.31815 |
| 40% | y = 0.025831 x − 1.0137 |
| 45% | y = 0.021752 x − 0.80945 |
| 50% | y = 0.018322 x − 0.7054 |
| 55% | y = 0.015539 x − 0.70155 |

The correction factors derived in this manner were used to recalibrate the measured glucose level with respect to the whole blood having 40% hematocrit level, resulting in the biosensors that provide hematocrit independent glucose concentrations. The meter reads the speed of sample introduction first and determines the level of hematocrit in the blood sample, looks up the table that provides the corresponding calibration curves, and determines the level of glucose from the measured currents. Table 3 shows the results of the experiment carried out as outlined.

TABLE 3

Glucose concentration in whole blood; the sample introducing speed measured with the fluidity determining electrode and the calibration curve in Table 2 were used to estimate the glucose level in whole blood.

| Hematocrit % | Glucose YSI2300 (mg/dL) | Hematocrit corrected (mg/dL) |
|---|---|---|
| 30% | 111 | 117 |
|  | 202 | 186 |
|  | 381 | 392 |
| 35% | 138 | 141 |
|  | 200 | 207 |
|  | 276 | 277 |
| 40% | 107 | 112 |
|  | 196 | 195 |
|  | 266 | 264 |
| 45% | 103 | 105 |
|  | 190 | 189 |
|  | 367 | 363 |
| 50% | 102 | 107 |
|  | 142 | 143 |
|  | 253 | 256 |
| 55% | 125 | 144 |
|  | 241 | 240 |
|  | 332 | 331 |

The fluidity determining electrode also discriminate the blood samples of unusual fluidity, i.e., samples with too high or too low hematocrit levels and the fouled introduction of blood samples due to the formation of air bubble. In such cases a measuring device may be programmed to issue a warning message or error code for the measurement.

EXPERIMENTAL EXAMPLE 4

Reduced Hematocrit Interference by Fatty Acid-Containing Reagent Layer

Biosensor strips were prepared as described in Example 4. Whole blood samples treated with heparin were centrifuged to separate the plasma and hematocrits, and remixed to obtain the blood samples of three different levels of hematocrits (20, 40 and 60%). The effect of hematocrits on the glucose measurement was evaluated at three different glucose concentrations with the biosensors prepared with the reagent layer of Example 1 and Example 2. The results are listed in Table 4 and 5. It is apparent that the biosensors prepared with the reagent of Example 2 result in substantially reduced hematocrit effect, providing the relative error with respect to 40% hematocrit level within clinically acceptable range.

TABLE 4

Hematocrit effect on the glucose measurement with the biosensors prepared with the reagent layer of Example 1

| Sample | 1 | | | 2 | | | 3 | | |
|---|---|---|---|---|---|---|---|---|---|
| Hematocrit level | 20 | 40 | 60 | 20 | 40 | 60 | 20 | 40 | 60 |
| YSI Glucose level (mg/dL) | 137 | 126 | 113 | 264 | 238 | 228 | 389 | 377 | 339 |
| Example 1 Reagent based biosensor | 175 | 125 | 88 | 365 | 231 | 146 | 544 | 369 | 114 |
| Bias % relative to 40% hematocrit level* | 29 | 0 | −22 | 42 | 0 | −34 | 43 | 0 | −66 |

*% Bias relative to 40% hematocrit level = {(glucose level by the biosensor/glucose level by YSI)/(glucose level by the biosensor at 40% hematocrit/glucose level by YSI at 40% hematocrit) − 1} × 100.

TABLE 5

Hematocrit effect on the glucose measurement with the biosensors prepared with the reagent layer of Example 2

| Sample | 1 | | | 2 | | | 3 | | |
|---|---|---|---|---|---|---|---|---|---|
| Hematocrit level | 20 | 40 | 60 | 20 | 40 | 60 | 20 | 40 | 60 |
| YSI Glucose level (mg/dL) | 120 | 111 | 107 | 212 | 199 | 191 | 435 | 398 | 374 |
| Example 2 Reagent based biosensor | 133 | 114 | 99 | 241 | 201 | 185 | 423 | 382 | 334 |
| Bias % relative to 40% hematocrit level* | 8 | 0 | −10 | 13 | 0 | −4 | 1 | 0 | −7 |

The results summarized in table 5 show that the biosensor based on example 2 reagents exhibits substantially reduced interfering responses to varying hematocrit levels (from 20% to 60%), whose measurement biases are less than 10% relative to 40% hematocrit level.

Examples are described in terms of the preferred embodiment of present invention. However, it should not be understood that such disclosure is limited to explicit description of present invention. The description and the claims of present invention are to be interpreted as covering all alterations and modifications within the true scope of this invention.

What is claimed is:

1. An electrochemical biosensor comprising:
   a lower substrate;
   an upper substrate;
   a working electrode and a reference (or counter) electrode respectively formed on either the lower substrate or the upper substrate;
   a reaction layer containing a glucose oxidase enzyme, electron transfer mediator, water soluble polymers, water soluble fatty acid or its salt, and quaternary ammonium salt, wherein the reaction layer is formed over the working electrode and is not formed over the reference electrode;
   a spacer formed between the lower and the upper substrates, wherein the spacer is provided with a cut out pattern of a sample introducing bay, an air discharge channel, and a void at the cross of a sample introducing bay and an air discharge channel; and
   wherein the electrochemical biosensor is capable of analyzing a whole blood sample.

2. The biosensor according to claim 1, wherein the working electrode and the reference electrode are formed on the same substrate.

3. The biosensor according to claim 1, wherein the working electrode and the reference electrode are formed on different substrates.

4. The biosensor according to claim 1, further comprising a fluidity determining electrode on the lower substrate, wherein the fluidity determining electrode is used to correct a hematocrit level-dependent measurement bias.

5. The biosensor according to claim 1, wherein the fatty acid or its salt has an alkyl chain of 4~20 carbons and is added in a range of 0.1 to 20 weight percent of all components.

6. The biosensor according to claim 1, wherein fatty acid is selected from the group consisting of saturated fatty acid, caproic acid, heptanoic acid, caprylic acid, nonanoic acid, capric acid, undecanoic acid, lauric acid, tridecanoic acid, myristic acid, pentadecanoic acid, palmitic acid, hepadecanoic acid, stearic acid, nonadecanoic acid, and arachidic acid.

7. The biosensor according to claim 1, wherein said fatty acid results in the effect of reducing the measurement bias arising from hematocrits.

8. The biosensor according to claim 1, wherein said reaction layer further contains quaternary ammonium salt in 0.1-30 wt % of all components.

9. The biosensor according to claim 8, wherein the quaternary ammonium salt is selected from the group consisting of the halide compounds of dodecyltrimethylammonium, myristyltrimethylammonium, cetyltrimethylammonium, octadecyltrimethylammonium and tetrahexylammonium.

10. The biosensor according to claim 1, wherein the electron transfer mediator is selected from the group consisting of hexaamineruthenium (III) chloride, potassium ferricyanide, potassium ferrocyanide, dimethylferrocene, ferricinium, ferocene-monocarboxylic acid, 7,7,8,8-tetracyanoquinodimethane, tetrathiafulvalene, nickelocene, N-methylacridinium, tetrathiatetracene, N-methylphenazinium, hydroquinone, 3-dimethylaminobenzoic acid, 3-methyl-2-benzothiazolinone hydrazone, 2-methoxy-4-allylphenol, 4-aminoantipyrin, dimethylaniline, 4-aminoantipyrene, 4-methoxynaphthol, 3,3',5,5'-tetramethylbenzidine, 2,2-azino-di-[3-ethylbenzthiazoline sulfonate], o-dianisidine, o-toluidine, 2,4-dichloro phenol, 4-aminophenazone, and benzidine and Prussian blue.

11. The biosensor according to claim 10, wherein the electron transfer mediator is hexaamineruthenium (III) chloride.

12. The according to claim 1, wherein the water soluble polymers are used to disperse and stabilize the enzyme and selected from the group consisting of polyvinyl pyrrolidone (PVP), polyvinyl alcohol (PVA), perfluoro sulfonate, hydroxyethyl cellulose (HEC), hydroxypropy cellulose (HPC), carboxy methyl cellulose (CMC), cellulose acetate, dextran, and polyamide.

13. The biosensor according to claim 1, wherein the ratio of the width of the air discharge channel to that of the sample introducing bay is no more than 1:2.

14. The biosensor according to claim 1, wherein the sample introducing bay has a capacity to hold 0.1-1.0 μl of liquid sample.

15. The biosensor according to claim 1, wherein the sample introducing bay is crossed with the air discharge channel at an angle of 75-105° and the void is provided from the crossing point to the bay end.

16. The biosensor according to claim 1, further comprising a viewing window on the upper substrate, which is located at the crossing cover of the sample channel.

* * * * *